(12) United States Patent
Farber

(10) Patent No.: US 7,807,716 B2
(45) Date of Patent: Oct. 5, 2010

(54) NITRIC OXIDE AMINO ACID ESTER COMPOUND, COMPOSITIONS FOR INCREASING NITRIC OXIDE LEVELS AND METHOD OF USE

(75) Inventor: Michael Farber, Montreal (CA)

(73) Assignee: Oral Delivery Technology Ltd., Montreal, Quebec (CA)

( * ) Notice: Subject to any disclaimer, the term of this patent is extended or adjusted under 35 U.S.C. 154(b) by 0 days.

(21) Appl. No.: 12/565,347

(22) Filed: Sep. 23, 2009

(65) Prior Publication Data

US 2010/0076043 A1 Mar. 25, 2010

Related U.S. Application Data

(60) Provisional application No. 61/099,621, filed on Sep. 24, 2008.

(51) Int. Cl.
*A61K 31/221* (2006.01)
*C07C 229/08* (2006.01)

(52) U.S. Cl. ....................... 514/551; 560/170
(58) Field of Classification Search ........................ None
See application file for complete search history.

(56) References Cited

U.S. PATENT DOCUMENTS

| | | | |
|---|---|---|---|
| 5,591,758 A | 1/1997 | Nallet et al. | |
| 5,807,847 A | 9/1998 | Thatcher et al. | |
| 5,932,538 A | 8/1999 | Garvey et al. | |
| 6,310,052 B1 | 10/2001 | Thatcher et al. | |
| 6,417,162 B1 | 7/2002 | Garvey et al. | |
| 6,433,182 B1 | 8/2002 | Garvey et al. | |
| 6,469,065 B1 | 10/2002 | Garvey et al. | |
| 6,514,934 B1 | 2/2003 | Garvey et al. | |
| 6,869,974 B1 | 3/2005 | Del Soldato | |
| 6,916,835 B2 | 7/2005 | Thatcher et al. | |
| 7,115,661 B1 | 10/2006 | Thatcher et al. | |
| 7,166,605 B2 | 1/2007 | Del Soldato et al. | |
| 7,166,638 B2 | 1/2007 | Benedini et al. | |
| 7,199,141 B2 | 4/2007 | Del Soldato et al. | |
| 7,273,946 B2 | 9/2007 | Ongini et al. | |
| 7,297,808 B2 | 11/2007 | Benedini et al. | |
| 7,345,053 B2 | 3/2008 | Garvey | |
| 7,378,412 B2 | 5/2008 | Del Soldato | |
| 7,449,469 B2 | 11/2008 | Ongini et al. | |
| 7,462,716 B2 | 12/2008 | Benedini et al. | |
| 7,563,909 B2 | 7/2009 | Benedini et al. | |
| 2006/0106082 A1 | 5/2006 | Del Soldato et al. | |
| 2007/0037821 A1 | 2/2007 | Garvey et al. | |

FOREIGN PATENT DOCUMENTS

WO   WO 2008/095841   *   8/2008

OTHER PUBLICATIONS

"Derivative." Merriam-Webster Online Dictionary. 2010. Merriam-Webster Online. Accessed Apr. 20, 2010. <http://merriam-webster.com/dictionary/derivative>.*
"Nutrex Hemo Rage Black," Product description and retail at BulkNutrition.com Accessed Apr. 19, 2010. < http://www.bulknutrition.com/?products_id=8107>.*
"MuscleMeds eNOXIDE," Item# 16041. Product description at SameDaySupplements.com:Supplement Your Health! Accessed Apr. 19, 2010. < http://www.samedaysupplements.com/musclemeds-enoxide-tabs-biomedical-nitric-oxide-p-16041.html>.*

* cited by examiner

*Primary Examiner*—Kamal A Saeed
*Assistant Examiner*—Alicia L Otton
(74) *Attorney, Agent, or Firm*—Klauber & Jackson LLC

(57) ABSTRACT

There is provided novel amino acid ester compounds comprising at least one nitric oxide releasing group and pharmaceutically acceptable salts thereof, and novel compositions comprising at least one amino acid ester compound comprising at least one nitric oxide releasing group, and, optionally, at least one nitric oxide donor and/or at least one therapeutic agent. Also provided are compositions for increasing nitric oxide physiological levels in a subject, methods for increasing nitric oxide physiological levels in a subject, methods for improving a subject's muscle strength, athletic performances and/or lean body mass gain and or performance in a subject.

12 Claims, No Drawings

NITRIC OXIDE AMINO ACID ESTER COMPOUND, COMPOSITIONS FOR INCREASING NITRIC OXIDE LEVELS AND METHOD OF USE

BACKGROUND (a) Field

The subject matter disclosed generally relates to novel amino acid ester compounds comprising at least one nitric oxide releasing group and pharmaceutically acceptable salts thereof, and novel compositions comprising at least one amino acid ester compound comprising at least one nitric oxide releasing group. The subject matter herein disclosed further relates to compositions for increasing nitroxic acid physiological levels in a subject, method for increasing nitric oxide levels in a subject, methods for improving a muscle strength, athletic performances and/or lean body mass gain and or endurance in a subject.

The nitric oxide releasing group is preferably a nitro group (i.e. $NO_2$), a nitroso group (i.e. NO) and/or a heterocyclic nitric oxide donor group. The aliphatic nitric oxide donor group is preferably:

$(CH_2)_n$—$ONO_2$ but can be aromatic or combinations thereof.

(b) Related Prior Art

Agents such as L-arginine, citrulline, yohimbine, norvaline, etc., have been used to induce higher nitric oxide levels and/or vasodilatation in subjects in an attempt to increase blood flow to muscles just prior, during or immediately after physical exercise or athletic performance.

It is believed that increased vasodilatation will result in increased blood flow to muscles during exercise resulting in higher oxygen, nutrient uptake and higher rate of removal of waste products.

SUMMARY

In a first embodiment there is a disclosed novel amino acid ester compound comprising at least one nitric oxide releasing group and pharmaceutically acceptable salts thereof. The nitric oxide releasing groups are preferably nitro groups (i.e. $NO_2$), nitroso groups (i.e. NO) and/or heterocyclic nitric oxide donor groups that are linked to the amino acid ester compounds through one or more sites such as oxygen (hydroxyl condensation), sulfur (sulfhydryl condensation) and/or nitrogen. The heterocyclic nitric oxide donor groups are preferably furoxans, sydnonimines, oxatriazole-5-ones and/or oxatriazole-5-imines.

The subject matter herein disclosed further relates to compositions for increasing nitric oxide physiological levels in a subject, methods for increasing nitric oxide physiological levels in a subject, methods for improving muscle strength, athletic performances and/or lean body mass gain.

The subject matter is also based on the discovery that administering at least one amino acid ester compound comprising at least one nitric oxide releasing group, or pharmaceutically acceptable salts thereof, can be used for the delivery of nitric oxide at the targeted site. Nitric oxide donors include, for example, S-nitrosothiols, nitrites, nitrates, N-oxo-N-nitrosamines, SPM 3672, SPM 5185, SPM 5186 and analogues thereof, and substrates of the various isozymes of nitric oxide synthase. Thus, another embodiment of the invention provides compositions comprising at least one amino acid ester compound comprising a nitric oxide releasing group. The invention also provides for such compositions in a pharmaceutically acceptable carrier. The nitric oxide releasing groups are preferably nitro groups (i.e. $NO_2$), nitroso groups (i.e. NO) and/or heterocyclic nitric oxide donor groups. The nitric oxide releasing group is preferably $(CH_2)_n$—$ONO_2$.

The invention provides compositions comprising at least one amino acid ester compound comprising at least one nitric oxide releasing group, and, optionally, at least one nitric oxide donor compound.

The method optionally further comprises the administration of at least one nitric oxide donor compound. In this embodiment of the invention, the methods can involve (i) administering the amino acid ester compounds comprising at least one nitric oxide releasing group, (ii) administering the amino acid ester compound comprising at least one nitric oxide releasing group, and others vasodilators, (iii) administering the amino acid ester compound comprising at least one nitric oxide releasing group or (iv) administering the amino acid ester compound comprising at least one nitric oxide releasing group and others vasodilators.

Another embodiment of the invention provides kits comprising at least one amino acid ester compound comprising at least one nitric oxide releasing group, and, optionally, at least one vasodilator donor compound. The amino acid ester compound comprising at least one nitric oxide releasing group and/or the nitric oxide donor can be separate components in the kit or can be in the form of a composition in one or more pharmaceutically acceptable carriers.

These and other aspects of the invention are described in detail herein.

The following terms are defined below.

"Amino acid ester compound" is intended to mean the condensation product of an amino acid with mononitrated alkane ou alkene diol. As will be evident to those familiar to the art, the condensation reaction could also involve, but not limited to, dipeptides or tripeptides, nitrated alcohols containing aliphatic, alkyl or aromatic moieties, as well as other nitric oxide groups attached to the alkane or alkene diols. Amino acid or dipeptide reactions are preferred as well as the condensation reaction with short chain mononitrated alkane diols such as 1,3 propanediol or 1,4 butanediol.

"Therapeutically effective amount" is intended to mean the amount of the compound and/or composition that is effective to achieve its intended purpose.

"Transdermal" is intended to mean the delivery of a compound by passage through the skin and into the blood stream.

"Transmucosal" is intended to mean the delivery of a compound by passage of the compound through the mucosal tissue and into the blood stream.

"Penetration enhancement" or "permeation enhancement" is intended to mean an increase in the permeability of the skin or mucosal tissue to a selected pharmacologically active compound such that the rate at which the compound permeates through the skin or mucosal tissue is increased.

"Carriers" or "vehicles" are intended to mean carrier materials suitable for compound administration and include any such material known in the art such as, for example, any liquid, gel, solvent, liquid diluent, solubilizer, or the like, which is non-toxic and which does not interact with any components of the composition in a deleterious manner.

"Sustained release" is intended to mean the release of a therapeutically active compound and/or composition such that the blood levels of the therapeutically active compound are maintained within a desirable therapeutic range over a period of time. The sustained release formulation can be prepared using any conventional method known to one skilled in the art to obtain the desired release characteristics.

"Nitric oxide adduct" or "NO adduct" is intended to mean compounds and functional groups which, under physiological conditions, can donate, release and/or directly or indirectly transfer any of the three redox forms of nitrogen monoxide ($NO^+$, $NO^-$, $NO^{\cdot}$), such that the biological activity of the nitrogen monoxide species is expressed at the intended site of action.

"Nitric oxide releasing" or "nitric oxide donating" is intended to mean methods of donating, releasing and/or directly or indirectly transferring any of the three redox forms of nitrogen monoxide (NO+, NO−, $NO^{\cdot}$), such that the biological activity of the nitrogen monoxide species is expressed at the intended site of action.

"Nitric oxide donor" or "NO donor" is intended to mean compounds that donate, release and/or directly or indirectly transfer a nitrogen monoxide species, and/or stimulate the endogenous production of nitric oxide or endothelium-derived relaxing factor (EDRF) in vivo and/or elevate endogenous levels of nitric oxide or EDRF in vivo and/or are oxidized to produce nitric oxide and/or are substrates for nitric oxide synthase and/or cytochrome P450. "NO donor" also includes compounds that are precursors of L-arginine, inhibitors of the enzyme arginase and nitric oxide mediators.

"Heterocyclic nitric oxide donor" is intended to mean a tri-substituted 5-membered ring comprising two or three nitrogen atoms and at least one oxygen atom. The heterocyclic nitric oxide donor is capable of donating and/or releasing a nitrogen monoxide species upon decomposition of the heterocyclic ring. Exemplary heterocyclic nitric oxide donors include oxatriazol-5-ones, oxatriazol-5-imines, sydnonimines, furoxans, and the like.

"Alkyl" is intended to mean a lower alkyl group, a substituted lower alkyl group, a haloalkyl group, a hydroxyalkyl group, an alkenyl group, a substituted alkenyl group, an alkynyl group, a bridged cycloalkyl group, a cycloalkyl group or a heterocyclic ring, as defined herein. An alkyl group may also comprise one or more radical species, such as, for example a cycloalkylalkyl group or a heterocyclicallyl group.

"Lower alkyl" is intended to mean a branched or straight chain acyclic alkyl group comprising one to about ten carbon atoms (preferably one to about eight carbon atoms, more preferably one to about six carbon atoms). Exemplary lower alkyl groups include methyl, ethyl, n-propyl, isopropyl, n-butyl, isobutyl, sec-butyl, t-butyl, pentyl, neopentyl, iso-amyl, hexyl, octyl, and the like.

"Substituted lower alkyl" is intended to mean a lower alkyl group, as defined herein, wherein one or more of the hydrogen atoms have been replaced with one or more $R^{100}$ groups, wherein each $R^{100}$ is independently a hydroxy, an ester, an amidyl, an oxo, a carboxyl, a carboxamido, a halo, a cyano, a nitrate or an amino group, as defined herein.

"Haloalkyl" is intended to mean a lower alkyl group, an alkenyl group, an alkynyl group, a bridged cycloalkyl group, a cycloalkyl group or a heterocyclic ring, as defined herein, to which is appended one or more halogens, as defined herein. Exemplary haloalkyl groups include trifluoromethyl, chloromethyl, 2-bromobutyl, 1-bromo-2-chloro-pentyl, and the like.

"Alkenyl" is intended to mean a branched or straight chain $C_2$-$C_{10}$ hydrocarbon (preferably a $C_2$-$C_8$ Ce hydrocarbon, more preferably a $C_2$-$C_6$ hydrocarbon) that can comprise one or more carbon-carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Lower alkenyl" is intended to mean a branched or straight chain $C_2$-$C_4$ hydrocarbon that can comprise one or two carbon-carbon double bonds.

"Substituted alkenyl" is intended to mean a branched or straight chain $C_2$-$C_{10}$ hydrocarbon (preferably a $C_2$-$C_8$; hydrocarbon, more preferably a $C_2$-$C_6$ hydrocarbon) which can comprise one or more carbon-carbon double bonds, wherein one or more of the hydrogen atoms have been replaced with one or more $R^{100}$ groups, wherein each $R^{100}$ is independently a hydroxy, an oxo, a carboxyl, a carboxamido, a halo, a cyano or an amino group, as defined herein.

"Alkynyl" is intended to mean an unsaturated acyclic $C_2$-$C_{10}$ to-hydrocarbon (preferably a $C_2$-$C_8$ hydrocarbon, more preferably a $C_2$-$C_6$ hydrocarbon) that can comprise one or more carbon-carbon triple bonds. Exemplary alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethyl-butyn-1-yl, and the like.

"Bridged cycloalkyl" is intended to mean two or more cycloalkyl groups, heterocyclic groups, or a combination thereof fused via adjacent or non-adjacent atoms. Bridged cycloalkyl groups can be unsubstituted or substituted with one, two or three substituents independently selected from alkyl, alkoxy, amino, alkylamino, dialkylamino, hydroxy, halo, carboxyl, alkylcarboxylic acid, aryl, amidyl, ester, alkylcarboxylic ester, carboxamido, alkylcarboxamido, oxo and nitro. Exemplary bridged cycloalkyl groups include adamantyl, decahydronapthyl, quinuclidyl, 2,6-dioxabicyclo(3,3,0)octane, 7-oxabicyclo(2,2,1)heptyl, 8-azabicyclo(3,2,1)oct-2-enyl and the like.

"Cycloalkyl" is intended to mean a saturated or unsaturated cyclic hydrocarbon comprising from about 3 to about 10 carbon atoms. Cycloalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo, alkylsulfinyl, and nitro. Exemplary cycloalkyl groups include cyclopropyl, cyclobutyl, cyclopentyl, cyclohexyl, cyclohexenyl, cyclohepta-1,3-dienyl, and the like.

"Heterocyclic ring or group" is intended to mean a saturated or unsaturated cyclic hydrocarbon group having about 2 to about 10 carbon atoms (preferably about 4 to about 6 carbon atoms) where 1 to about 4 carbon atoms are replaced by one or more nitrogen, oxygen and/or sulfur atoms. Sulfur may be in the thio, sulfinyl or sulfonyl oxidation state. The heterocyclic ring or group can be fused to an aromatic hydrocarbon group. Heterocyclic groups can be unsubstituted or substituted with one, two or three substituents independently selected from alkyl, alkoxy, amino, alkylthio, aryloxy, arylthio, arylalkyl, hydroxy, oxo, thial, halo, carboxyl, carboxylic ester, alkylcarboxylic acid, alkylcarboxylic ester, aryl, arylcarboxylic acid, arylcarboxylic ester, amidyl, ester, alkylcarbonyl, arylcarbonyl, alkylsulfinyl, carboxamido, alkylcarboxamido, arylcarboxamido, sulfonic acid, sulfonic ester, sulfonamide nitrate and nitro. Exemplary heterocyclic groups include pyrrolyl, furyl, thienyl, 3-pyrrolinyl, 4,5,6-trihydro-2H-pyranyl, pyridinyl, 1,4-dihydropyridinyl, pyrazolyl, triazolyl, pyrimidinyl, pyridazinyl, oxazolyl, thiazolyl, imidazolyl, indolyl, thiophenyl, furanyl, tetrahydrofuranyl, tetrazolyl, pyrrolinyl, pyrrolindinyl, oxazolindinyl 1,3-dioxolanyl, imidazolinyl, imidazolindinyl, pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5- trithianyl, benzo(b)thiophenyl, benzimidazolyl, benzothiazolinyl, quinolinyl, 2,6-dioxabicyclo(3,3,0)octane, and the like.

"Heterocyclic compounds" is intended to mean mono- and polycyclic compounds comprising at least one aryl or heterocyclic ring.

"Aryl" is intended to mean a monocyclic, bicyclic, carbocyclic or heterocyclic ring system comprising one or two aromatic rings. Exemplary aryl groups include phenyl, pyridyl, napthyl, quinoyl, tetrahydronaphthyl, furanyl, indanyl, indenyl, indoyl, and the like. Aryl groups (including bicyclic aryl groups) can be unsubstituted or substituted with one, two or three substituents independently selected from alkyl, alkoxy, alkylthio, amino, alkylamino, dialkylamino, arylamino, diarylamino, alkylarylamino, halo, cyano, alkylsulfinyl, hydroxy, carboxyl, carboxylic ester, alkylcarboxylic acid, alkylcarboxylic ester, aryl, arylcarboxylic acid, arylcarboxylic ester, alkylcarbonyl, arylcarbonyl, amidyl, ester, carboxamido, alkylcarboxamido, carbomyl, sulfonic acid, sulfonic ester, sulfonamido and nitro. Exemplary substituted aryl groups include tetrafluorophenyl, pentafluorophenyl, sulfonamide, alkylsulfonyl, arylsulfonyl, and the like.

"Cycloalkenyl" is intended to mean an unsaturated cyclic $C_2$-$C_{10}$ hydrocarbon (preferably a $C_2$-$C_8$ hydrocarbon, more preferably a $C_2$-$C_6$ hydrocarbon), which can comprise one or more carbon-carbon triple bonds.

"Alkylaryl" is intended to mean an alkyl group, as defined herein, to which is appended an aryl group, as defined herein. Exemplary alkylaryl groups include benzyl, phenylethyl, hydroxybenzyl, fluorobenzyl, fluorophenylethyl, and the like.

"Arylalkyl" is intended to mean an aryl radical, as defined herein, attached to an alkyl radical, as defined herein. Exemplary arylalkyl groups include benzyl, phenylethyl, 4-hydroxybenzyl, 3-fluorobenzyl, 2-fluorophenylethyl, and the like.

"Arylalkenyl" is intended to mean an aryl radical, as defined herein, attached to an alkenyl radical, as defined herein. Exemplary arylalkenyl groups include styryl, propenylphenyl, and the like.

"Cycloalkylalkyl" is intended to mean a cycloalkyl radical, as defined herein, attached to an alkyl radical, as defined herein.

"Cycloalkylalkoxy" is intended to mean a cycloalkyl radical, as defined herein, attached to an alkoxy radical, as defined herein.

"Cycloalkylalkylthio" is intended to mean a cycloalkyl radical, as defined herein, attached to an alkylthio radical, as defined herein.

"Heterocyclicalkyl" is intended to mean a heterocyclic ring radical, as defined herein, attached to an alkyl radical, as defined herein.

"Arylheterocyclic ring" is intended to mean a bi- or tricyclic ring comprised of an aryl ring, as defined herein, appended via two adjacent carbon atoms of the aryl ring to a heterocyclic ring, as defined herein. Exemplary arylheterocyclic rings include dihydroindole, 1,2,3,4-tetra-hydroquinoline, and the like.

"Alkylheterocyclic ring" is intended to mean a heterocyclic ring radical, as defined herein, attached to an alkyl radical, as defined herein. Exemplary alkylheterocyclic rings include 2-pyridylmethyl, 1-methylpiperidin-2-one-3-methyl, and the like.

"Alkoxy" is intended to mean $R_{50}O$—, wherein $R_{50}$ is an alkyl group, as defined herein (preferably a lower alkyl group or a haloalkyl group, as defined herein). Exemplary alkoxy groups include methoxy, ethoxy, t-butoxy, cyclopentyloxy, trifluoromethoxy, and the like.

"Aryloxy" is intended to mean $R_{55}$—O—, wherein $R_{55}$ is an aryl group, as defined herein. Exemplary arylkoxy groups include napthyloxy, quinolyloxy, isoquinolizinyloxy, and the like.

"Alkylthio" is intended to mean $R_{50}S$—, wherein $R_{50}$ is an alkyl group, as defined herein.

"Lower alkylthio" is intended to mean a lower alkyl group, as defined herein, appended to a thio group, as defined herein.

"Arylalkoxy" or "alkoxyaryl" is intended to mean an alkoxy group, as defined herein, to which is appended an aryl group, as defined herein. Exemplary arylalkoxy groups include benzyloxy, phenylethoxy, chlorophenylethoxy, and the like.

"Arylalklythio" is intended to mean an alkylthio group, as defined herein, to which is appended an aryl group, as defined herein. Exemplary arylalklythio groups include benzylthio, phenylethylthio, chlorophenylethylthio, and the like.

"Arylalklythioalkyl" is intended to mean an arylalkylthio group, as defined herein, to which is appended an alkyl group, as defined herein. Exemplary arylalklythioallyl groups include benzylthiomethyl, phenylethylthiomethyl, chlorophenylethylthioethyl, and the like.

"Alkylthioalkyl" is intended to mean an alkylthio group, as defined herein, to which is appended an alkyl group, as defined herein. Exemplary alkylthioalkyl groups include allylthiomethyl, ethylthiomethyl, trifluoroethylthiomethyl, and the like.

"Alkoxyalkyl" is intended to mean an alkoxy group, as defined herein, appended to an alkyl group, as defined herein. Exemplary alkoxyalkyl groups include methoxymethyl, methoxyethyl, isopropoxymethyl, and the like.

"Alkoxyhaloalkyl" is intended to mean an alkoxy group, as defined herein, appended to a haloalkyl group, as defined herein. Exemplary alkoxyhaloalkyl groups include 4-methoxy-2-chlorobutyl and the like.

"Cycloalkoxy" is intended to mean $R_{54}O$—, wherein $R_{54}$ is a cycloalkyl group or a bridged cycloalkyl group, as defined herein. Exemplary cycloalkoxy groups include cyclopropyloxy, cyclopentyloxy, cyclohexyloxy, and the like.

"Cycloalkylthio" is intended to mean $R_{54}S$, wherein $R_{54}$ is a cycloalkyl group or a bridged cycloalkyl group, as defined herein. Exemplary cycloalkylthio groups include cyclopropylthio, cyclopentylthio, cyclohexylthio, and the like.

"Haloalkoxy" is intended to mean an alkoxy group, as defined herein, in which one or more of the hydrogen atoms on the alkoxy group are substituted with halogens, as defined herein.

Exemplary haloalkoxy groups include 1,1,1-trichloroethoxy, 2-bromobutoxy, and the like.

"Hydroxy" is intended to mean —OH.

"Oxy" is intended to mean —O—

"Oxo" is intended to mean =O.

"Oxylate" is intended to mean —O—$R_{77}^+$, wherein $R_{77}$ is an organic or inorganic cation.

"Thiol" is intended to mean —SH.

"Thio" is intended to mean —S—.

"Oxime" is intended to mean =N—$OR_{81}$ wherein $R^{81}$ is a hydrogen, an alkyl group, an aryl group, an alkylsulfonyl group, an arylsulfonyl group, a carboxylic ester, an alkylcarbonyl group, an arylcarbonyl group, a carboxamido group, an alkoxyalkyl group or an alkoxyaryl group.

"Hydrazone is intended to mean =N—N($R_{81}$)($R'_{81}$), wherein $R'_{81}$ is independently selected from $R_{81}$, and $R_{81}$, is as defined herein.

"Hydrazino" is intended to mean $H_2N$—N(H)—.

"Organic cation" is intended to mean a positively charged organic ion. Exemplary organic cations include alkyl substituted ammonium cations, and the like.

"Inorganic cation" is intended to mean a positively charged metal ion. Exemplary inorganic cations include Group I metal cations such as for example, sodium, potassium, magnesium, calcium, and the like.

"Hydroxyalkyl" is intended to mean a hydroxy group, as defined herein, appended to an alkyl group, as defined herein.

"Nitrate" is intended to mean —O—$NO_2$

"Nitrite" is intended to mean —O—NO.

"Thionitrate" is intended to mean —S—$NO_2$.

"Thionitrite" and "nitrosothiol" is intended to mean —S—NO.

"Nitro" is intended to mean the group —$NO_2$. And "nitrosated" refers to compounds that have been substituted therewith.

"Nitroso" is intended to mean the group-NO and "nitrosylated" refers to compounds that have been substituted therewith.

"Nitrile" and "cyano" is intended to mean —CN.

"Halogen" or "halo" is intended to mean iodine (I), bromine (Br), chlorine (Cl), and/or fluorine (F).

"Amino" refers to —$NH_2$, an alkylamino group, a dialkylamino group, an arylamino group, a diarylamino group, an alkylarylamino group or a heterocyclic ring, as defined herein.

"Alkylamino" is intended to mean $R_{50}NH$—, wherein $R_{50}$ is an alkyl group, as defined herein. Exemplary alkylamino groups include methylamino, ethylamino, butylamino, cyclohexylamino, and the like.

"Arylamino" is intended to mean $R_{55}NH$—, wherein $R_{55}$ is an aryl group, as defined herein.

"Dialkylamino" is intended to mean $R_{52}R_{53}N$—, wherein $R_{52}$ and $R_{53}$ are each independently an alkyl group, as defined herein. Exemplary dialkylamino groups include dimethylamino, diethylamino, methyl propargylamino, and the like.

"Diarylamino" is intended to mean $R_{55}R_{60}N$—, wherein $R_{55}$ and $R_{60}$ are each independently an aryl group, as defined herein.

"Alkylarylamino or arylalkylamino" is intended to mean $R_{52}R_{55}N$—, wherein $R_{52}$ is an alkyl group, as defined herein, and $R_{55}$ is an aryl group, as defined herein.

"Alkylarylalkylamino" is intended to mean $R_{52}R_{79}N$—, wherein $R_{52}$ is an alkyl group, as defined herein, and $R_{79}$ is an arylalkyl group, as defined herein.

"Alkylcycloalkylamino" is intended to mean $R_{52}R_{80}N$—, wherein $R_{52}$ is an alkyl group, as defined herein, and $R_{80}$ is an cycloalkyl group, as defined herein.

"Aminoalkyl" is intended to mean an amino group, an alkylamino group, a dialkylamino group, an arylamino group, a diarylamino group, an alkylarylamino group or a heterocyclic ring, as defined herein, to which is appended an alkyl group, as defined herein. Exemplary aminoalkyl groups include dimethylaminopropyl, diphenylaminocyclopentyl, methylaminomethyl, and the like.

"Aminoaryl" is intended to mean an aryl group to which is appended an alkylamino group, a arylamino group or an arylalkylamino group. Exemplary aminoaryl groups include anilino, N-methylanilino, N-benzylanilino, and the like.

"Thio" is intended to mean —S—.

"Sulfinyl" is intended to mean —S(O)—.

"Methanthial" is intended to mean —C(S)—.

"Thial" is intended to mean =S.

"Sulfonyl" is intended to mean —S(O)2.

"Sulfonic acid" is intended to mean —$S(O)_2OR_{76}$, wherein $R_{76}$ is a hydrogen, an organic cation or an inorganic cation, as defined herein.

"Alkylsulfonic acid" is intended to mean a sulfonic acid group, as defined herein, appended to an alkyl group, as defined herein.

"Arylsulfonic acid" is intended to mean a sulfonic acid group, as defined herein, appended to an aryl group, as defined herein.

"Sulfonic ester" refers to —$S(O)_2OR_{58}$, wherein $R_{58}$ is an alkyl group, an aryl group, or an aryl heterocyclic ring, as defined herein.

"Sulfonamido" is intended to mean —$S(O)_2$—$N(R_{51})$($R_{57}$), wherein $R_{51}$ and $R_{57}$ are each independently a hydrogen atom, an alkyl group, an aryl group or an arylheterocyclic ring, as defined herein, or $R_{51}$ and $R_{57}$ when taken together are a heterocyclic ring, a cycloalkyl group or a bridged cycloalkyl group, as defined herein.

"Alkylsulfonamido" is intended to mean a sulfonamido group, as defined herein, appended to an alkyl group, as defined herein.

"Arylsulfonamido" is intended to mean a sulfonamido group, as defined herein, appended to an aryl group, as defined herein.

"Alkylthio" is intended to mean $R_{50}S$—, wherein $R_{50}$ is an alkyl group, as defined herein (preferably a lower alkyl group, as defined herein).

"Arylthio" is intended to mean $R_{55}S$—, wherein $R_{55}$ is an aryl group, as defined herein.

"Arylalkylthio" is intended to mean an aryl group, as defined herein, appended to an alkylthio group, as defined herein.

"Alkylsulfinyl" is intended to mean $R_{50}$—S(O)—, wherein $R_{50}$ is an alkyl group, as defined herein.

"Alkylsulfonyl" is intended to mean $R_{50}$—$S(O)_2$—, wherein $R_{50}$ is an alkyl group, as defined herein.

"Alkylsulfonyloxy" is intended to mean $R_{50}$—$S(O)_2$—O—, wherein $R_{50}$ is an alkyl group, as defined herein.

"Arylsulfinyl" is intended to mean $R_{55}$—S(O)—, wherein $R_{55}$ is an aryl group, as defined herein.

"Arylsulfonyl", is intended to mean $R_{55}$—$S(O)_2$—, wherein $R_{55}$ is an aryl group, as defined herein.

"Arylsulfonyloxy" is intended to mean $R_{55}$—$S(O)_2$—O—, wherein $R_{55}$ is an aryl group, as defined herein.

"Amidyl" is intended to mean $R_{51}C(O)N(R_{57})$— wherein $R_{51}$ and $R_{57}$ are each independently a hydrogen atom, an alkyl group, an aryl group or an arylheterocyclic ring, as defined herein.

"Ester" is intended to mean $R_{51}C(O)R_{76}$— wherein $R_{51}$ is a hydrogen atom, an alkyl group, an aryl group or an arylheterocyclic ring, as defined herein and $R_{76}$ is oxygen or sulfur.

"Carbamoyl" is intended to mean —O—$C(O)N(R_{51})$($R_{57}$), wherein $R_{51}$ and $R_{57}$ are each independently a hydrogen atom, an alkyl group, an aryl group or an arylheterocyclic ring, as defined herein, or $R_{51}$ and $R_{57}$ taken together are a heterocyclic ring, a cycloalkyl group or a bridged cycloalkyl group, as defined herein.

"Carboxyl" is intended to mean —$C(O)OR_{76}$, wherein $R_{76}$ is a hydrogen, an organic cation or an inorganic cation, as defined herein.

"Carbonyl" refers to —C(O)—.

"Alkylcarbonyl" refers to $R_{52}$—C(O)—, wherein $R_{52}$ is an alkyl group, as defined herein.

"Arylcarbonyl" refers to $R_{55}$—C(O)—, wherein $R_{55}$ is an aryl group, as defined herein.

"Arylalkylcarbonyl" refers to $R_{55}$—$R_{52}$—C(O)—, wherein $R_{55}$ is an aryl group, as defined herein, and $R_{52}$ is an alkyl group, as defined herein.

"Alkylarylcarbonyl" refers to $R_{52}$—$R_{55}$—C(O)—, wherein $R_{52}$ is an aryl group, as defined herein, and $R_{55}$ is an alkyl group, as defined herein.

"Heterocyclicalkylcarbonyl" refer to $R_{78}$C(O)— wherein $R_{78}$ is a heterocycloalkyl group, as defined herein.

"Carboxylic ester" refers to —C(O)O$R_{58}$, wherein $R_{58}$ is an alkyl group, an aryl group or an aryl heterocyclic ring, as defined herein.

"Alkylcarboxylic acid" and "alkylcarboxyl" refer to an alkyl group, as defined herein, appended to a carboxyl group, as defined herein.

"Alkylcarboxylic ester" refers to an alkyl group, as defined herein, appended to a carboxylic ester group, as defined herein.

"Alkyl ester" refers to an alkyl group, as defined herein, appended to an ester group, as defined herein.

"Arylcarboxylic acid" refers to an aryl group, as defined herein, appended to a carboxyl group, as defined herein.

"Arylcarboxylic ester" and "arylcarboxyl" refer to an aryl group, as defined herein, appended to a carboxylic ester group, as defined herein.

"Aryl ester" refers to an aryl group, as defined herein, appended to an ester group, as defined herein.

"Carboxamido" refers to —C(O)N($R_{51}$)($R_{57}$), wherein $R_{51}$ and $R_{57}$ are each independently a hydrogen atom, an alkyl group, an aryl group or an arylheterocyclic ring, as defined herein, or $R_{51}$ and $R_{57}$ when taken together are a heterocyclic ring, a cycloalkyl group or a bridged cycloalkyl group, as defined herein.

"Alkylcarboxamido" refers to an alkyl group, as defined herein, appended to a carboxamido group, as defined herein.

"Arylcarboxamido" refers to an aryl group, as defined herein, appended to a carboxamido group, as defined herein.

"Urea" refers to —N($R_{59}$)—C(O)N($R_{51}$)($R_{57}$) wherein $R_{51}$, $R_{57}$, and $R_{59}$ are each independently a hydrogen atom, an alkyl group, an aryl group or an arylheterocyclic ring, as defined herein, or $R_{51}$ and $R_{57}$ taken together are a heterocyclic ring, a cycloalkyl group or a bridged cycloalkyl group, as defined herein.

"Phosphoryl" refers to —P($R_{70}$)($R_{71}$)($R_{72}$), wherein $R_{70}$ is a lone pair of electrons, thial or oxo, and $R_{71}$ and $R_{72}$ are each independently a covalent bond, a hydrogen, a lower alkyl, an alkoxy, an alkylamino, a hydroxy, an oxy or an aryl, as defined herein.

"Silyl" refers to —Si($R_{73}$)($R_{74}$)($R_{75}$), wherein $R_{73}$, $R_{74}$ and $R_{75}$ are each independently a covalent bond, a lower alkyl, an alkoxy, an aryl or an arylalkoxy, as defined herein.

"Supplement" is intended to mean a product (other than tobacco) that is intended to supplement the diet that bears or contains one or more of the following dietary ingredients: a vitamin, a mineral, an herb or other botanical, an amino acid, a dietary substance for use by man or animal (horse) to supplement the diet by increasing the total daily intake, or a concentrate, metabolite, constituent, extract, or combinations of these ingredients.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims.

Accordingly, the drawings and the description are to be regarded as illustrative in nature, and not as restrictive and the full scope of the subject matter is set forth in the claims.

DETAILED DESCRIPTION OF THE PREFERRED EMBODIMENTS

In embodiments there are disclosed compositions for increasing nitric oxide physiological levels in a subject, methods for increasing nitric oxide physiological levels in a subject, methods for improving a subject's muscle strength, athletic performances and/or lean body mass gain and/or endurance.

The novel compounds and novel compositions of the invention are described in more detail herein.

In embodiments the amino acid ester compounds comprising at least one nitric oxide releasing group, and pharmaceutically acceptable salts thereof, the compounds of Formula (I):

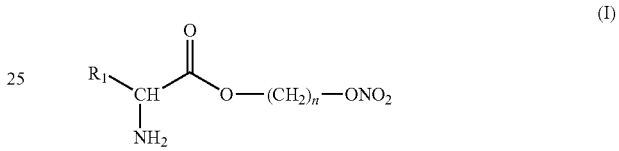

wherein, n=1 to 10;

$R_1$=an amino acid side chain group (D or L configuration), a modified amino acid side chain group (D or L configuration), and derivatives thereof.

Preferably, the compound of Formula (I) is

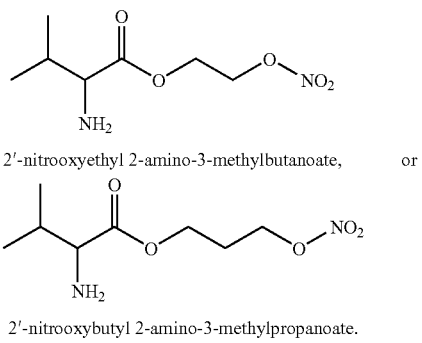

2'-nitrooxyethyl 2-amino-3-methylbutanoate, or

2'-nitrooxybutyl 2-amino-3-methylpropanoate.

In cases where multiple designations of variables which reside in sequence are chosen as a "covalent bond" or the integer chosen is 0, the intent is to denote a single covalent bond connecting one radical to another. For example, $E_0$ would denote a covalent bond, while $E_2$ denotes (E-E) and $(C(R_4)(R_4))_2$ denotes —$C(R_4)(R_4)$—$C(R_4)(R_4)$—.

Compounds of the invention that have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. It is to be understood that the invention anticipates and includes within its scope all such isomers and mixtures thereof.

Compounds of the invention that have one or more double bounds may exist as a single tautomers or a mixture of tautomers. It is to be understood that the invention anticipates and includes within its scope all such tautomers and mixtures thereof.

In another embodiment the amino acid ester compounds comprising at least one nitric oxide releasing group, and pharmaceutically acceptable salts thereof, the compounds of Formula II:

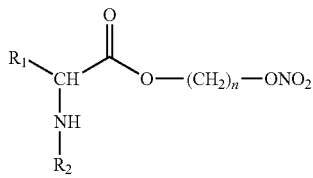

(II)

wherein, n=1 to 10;

$R_1$=—$CH_2CH_3$;

$R_2$=an amino acid side chain group (D or L configuration), a modified amino acid side chain group (D or L configuration) or derivatives thereof.

Another embodiment of the invention describes the metabolites of the amino acid ester compounds comprising a nitric oxide releasing group and pharmaceutically acceptable salts thereof. These metabolites, include but are not limited to, the non-nitrosated and/or nitrosylated derivatives, the non-heterocyclic nitric oxide donor derivatives, degradation products, hydrolysis products, and the like, of the amino acid ester compounds comprising at least one nitric oxide releasing group and pharmaceutically acceptable salts thereof.

Another embodiment of the invention provides processes for making the novel compounds of the invention and to the intermediates useful in such processes. The reactions are performed in solvents appropriate to the reagents and materials used are suitable for the transformations being effected. It is understood by one skilled in the art of organic synthesis that the functionality present in the molecule must be consistent with the chemical transformation proposed. This will, on occasion, necessitate judgment by the chemist as to the order of synthetic steps, protecting groups required, and deprotection conditions.

Substituents on the starting materials may be incompatible with some of the reaction conditions required in some of the methods described, but alternative methods and substituents compatible with the reaction conditions will be readily apparent to one skilled in the art. The use of sulfur and oxygen protecting groups is well known for protecting thiol and alcohol groups against undesirable reactions during a synthetic procedure and many such protecting groups are known and described by, for example, Greene and Wuts, *Protective Groups in Organic Synthesis*, Third Edition, John Wiley & Sons, New York (1999).

The chemical reactions described herein are generally disclosed in terms of their broadest application to the preparation of the compounds of this invention. Occasionally, the reactions may not be applicable as described to each compound included within the disclosed scope. The compounds for which this occurs will be readily recognized by one skilled in the art. In all such cases, either the reactions can be successfully performed by conventional modifications known to one skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials.

The amino acid esters compounds may be based on natural and modified amino acids, with side chain as presented herein. Any of the amino acids and their side chains could be modified at various reactive sites such for example carbon, amide, amine, carboxy, oxo, thio, hydroxyl sites, with extra attachments as are known in the art. Such attachments may include $(CH_2)_n$, $CH_3$, $O(CH_2)_n$, $OCH_3$, and other modifications well known in the art. These attachments may, for example, alter uptake, crossing of the blood brain barrier (when a glycosidic linkage is made to the amide) or other potentials applications. Also, the more lipophilic modifications may be used for transdermal crossing applications, which include but are not limited to anti-aging of the skin.

| N° | Originating Amino acid | formula | $R_1$ |
|---|---|---|---|
| 1 | Glycine | H | —H |
| 2 | Alanine | $CH_3$ | —$CH_3$ |
| 3 | Valine* | $(CH_3)_2$ | $CH_3$—CH—$CH_3$ |
| 4 | Leucine* | $CH_2CH(CH_3)_2$ | $CH_2$—CH($CH_3$)—$CH_3$ |
| 5 | Isoleucine* | $CH(CH_3)CH_2CH_3$ | HC($CH_3$)—$CH_2$—$CH_3$ |
| 6 | Phenylalanine* | $CH_2C_6H_5$ | $CH_2$—C6H5 (phenyl) |
| 7 | Tyrosine | $CH_2C_6H_4OH$ | $H_2C$—C6H4—OH |
| 8 | Tryptophane* | $C_9H_8N$ | $H_2C$—indolyl |
| 9 | Serine | $CH_2OH$ | $H_2C$—OH |
| 10 | Threonine* | $CH(OH)CH_3$ | HC($CH_3$)—OH |
| 11 | Cysteine | $CH_2SH$ | $H_2C$—SH |

-continued

| | Natural Amino Acids | | |
|---|---|---|---|
| N° | Originating Amino acid | formula | $R_1$ |
| 12 | Methionine* | $CH_2CH_2SCH_3$ | $H_2C-CH_2-S-CH_3$ |
| 13 | Proline | $C_5H_9NO_2$ | (pyrrolidine-2-carboxylic acid structure) |
| 14 | Asparagine | $CH_2COCH_2$ | $H_2C-\underset{\underset{O}{\|}}{C}-NH_2$ |
| 15 | Glutamine | $CH_2CH_2CONH_2$ | $H_2C-CH_2-\underset{\underset{O}{\|}}{C}-NH_2$ |
| 16 | Aspartic acid | $CH_2COOH$ | $CH_2-COOH$ |
| 17 | Glutamic acid | $CH_2CH_2COOH$ | $H_2C-CH_2-COOH$ |
| 18 | Lysine* | $CH_2CH_2CH_2CH_2NH_2$ | $H_2C-CH_2-CH_2 \mid H_2N-CH_2$ |
| 19 | Histidine* | $CH_3C_3N_2H_3$ | (imidazole-methyl structure) |
| 20 | Arginine* | $(CH_2)_3CN_3H_4$ | $H_2C-CH_2-CH_2 \mid H_2N-C-NH \mid NH$ |

*essential amino acids

| | Modified Amino Acids | | |
|---|---|---|---|
| N° | Originating Amino acid | Formula | $R_1$ |
| A | Cystine | $CH_2S_2CH_2CHNH_2COOH$ | $H_2C-S-S-CH_2 \mid H_2N-CH-COOH$ |
| B | Hydroxyproline | | (4-hydroxypyrrolidine-2-carboxylic acid) |
| C | ε-N-methyllysine | $CH_2CH_2CH_2CH_2NHCH_3$ | $H_2C-CH_2-CH_2-CH_2 \mid H_3C-NH$ |
| D | β-alanine | $NH_2CH_2CH_2COOH$ | $CH_2-CH_2-COOH \mid NH_2$ |
| E | diiodotyrosine | $CH_2C_6H_2I_2OH$ | (3,5-diiodo-4-hydroxyphenyl-methyl) |
| F | homocysteine | $CH_2CH_2SH$ | $H_2C-CH_2-SH$ |
| G | ornithine | $CH_2CH_2CH_2NH_2$ | $H_2C-CH_2-CH_2 \mid NH_2$ |
| H | Norvaline | $CH_2-CH_3$ | $CH_2-CH_3$ |
| I | selenocysteine | SeH | SeH |

-continued

Modified Amino Acids

| N° | Originating Amino acid | Formula | R$_1$ |
|---|---|---|---|
| J | Hypusine | CH$_2$CH$_2$CH$_2$CH$_2$NHCH$_2$CH(OH)CH$_2$CH$_2$NH$_2$ | H$_2$N–(CH$_2$)$_3$–CH(OH)–CH$_2$–NH–(CH$_2$)$_4$– |
| K | Dehydroalanine | CH$_2$ | H$_2$C= |

The amino acid ester compounds are nitrosated and/or nitrosylated through one or more sites such as oxygen, sulfur and/or nitrogen using conventional methods known to one skilled in the art. For example, known methods for nitrosating and/or nitrosylating compounds are described in U.S. Pat. Nos. 5,380,758, 5,859,053, 5,703,073 and 6,297,260; and in WO 94103421, WO 94/04484, WO 94/12463, WO 95/09831, WO 95/19952, WO 95/30641, WO 97/27749, WO 98/19672, WO 98/21193, WO 00/51988, WO 00/61604, WO 00/72838, WO 01/00563, WO 01/04082, WO 01/10814, WO 01/12584, WO 01/45703, WO 00/61541, WO 00/61537, WO 02/11707, WO 02/30866 and in Oae et al, Org. Prep. Proc. Int., 15 (3): 165-198 (1983), the disclosures of each of which are incorporated by reference herein in their entirety. The methods of nitrosating and/or nitrosylating the compounds described in these references can be applied by one skilled in the art to produce any of the nitrosated and/or nitrosylated amino acid ester compounds described herein. The nitrosated and/or nitrosylated amino acid ester compounds of the invention donate, transfer or release a biologically active form of nitrogen monoxide (i.e., nitric oxide).

Nitrogen monoxide can exist in three forms: NO$^-$ (nitroxyl), NO· (uncharged nitric oxide) and NO$^+$ (nitrosonium). NO· is a highly reactive short-lived species that is potentially toxic to cells. This is critical because the pharmacological efficacy of NO depends upon the form in which it is delivered. In contrast to the nitric oxide radical (NO·), nitrosonium (NO$^+$) does not react with O$_2$ or O$_2^-$ species and functionalities capable of transferring and/or releasing NO$^+$ and NO$^-$ are also resistant to decomposition in the presence of many redox metals. Consequently, administration of charged NO equivalents (positive and/or negative) is a more effective means of delivering a biologically active NO to the desired site of action.

Compounds contemplated for use in the invention, e.g., amino acid ester compounds that contain nitric oxide releasing group, linked through one or more sites such as oxygen (hydroxyl condensation), sulfur and/or nitrogen, are, optionally, used in combination with nitric oxide and compounds that release nitric oxide or otherwise directly or indirectly deliver or transfer a biologically active form of nitrogen monoxide to a site of its intended activity, such as on a cell membrane in vivo.

Nitrogen monoxide can exist in three forms: NO$^-$ (nitroxyl), NO· (nitric oxide) and NO$^+$ (nitrosonium). NO· is a highly reactive short-lived species that is potentially toxic to cells. This is critical because the pharmacological efficacy of NO depends upon the form in which it is delivered. In contrast to the nitric oxide radical (NO·), nitrosonium (NO$^+$) does not react with O$_2$ or O$_2^-$ species, and functionalities capable of transferring and/or releasing NO$^+$ and NO$^-$ are also resistant to decomposition in the presence of many redox metals. Consequently, administration of charged NO equivalents (positive and/or negative) does not result in the generation of toxic by-products or the elimination of the active NO group.

The term "nitric oxide" encompasses uncharged nitric oxide (NO·) and charged nitrogen monoxide species, preferably charged nitrogen monoxide species, such as nitrosonium ion (NO$^+$) and nitroxyl ion (NO$^-$). The reactive form of nitric oxide can be provided by gaseous nitric oxide. The nitrogen monoxide releasing, delivering or transferring compounds have the structure F—NO, wherein F is a nitrogen monoxide releasing, delivering or transferring group, and include any and all such compounds which provide nitrogen monoxide to its intended site of action in a form active for its intended purpose. The term "NO adducts" encompasses any nitrogen monoxide releasing, delivering or transferring compounds, including, for example, S-nitrosothiols, nitrites, nitrates, S-nitrothiols, sydnonimines, 2-hydroxy-2-nitrosohydrazines, (NONOates), (E)-alkyl-2-((E)-hydroxyimino)-5-nitro-3-hexeneamide (FK-409), (E)-alkyl-2-((E)-hydroxyimino)-5-nitro-3-hexeneamines, N-(4-ethyl-2-(hydroxyimino)-6-methyl-5-nitro-3-heptenyl)-3-pyridinecarboxamide (FR 146801), N-nitrosoamines, N-hydroxyl nitrosamines, nitrosimines, diazetine dioxides, oxatriazole 5-imines, oxatriazole 5-ones, oximes, hydroxylamines, N-hydroxyguanidines, hydroxyureas, benzofuroxanes, furoxans as well as substrates for the endogenous enzymes which synthesize nitric oxide.

Suitable NONOates include, but are not limited to, (Z)-1-(N-methyl-N-(6-(N-methyl-ammoniohexyl)amino))diazen-1-ium-1,2-diolate ("MAHMA/NO"), (Z)-1-(N-(3-ammoniopropyl)-N-(n-propyl)amino)diazen-1-ium-1,2-diolate ("PAPA/NO"), (Z)-1-(N-(3-aminopropyl)-N-(4-(3-aminopropylammonio)butylyamino)diazen-1-ium-1,2-diolate (spermine NONOate or "SPER/NO") and sodium (Z)-1-(N,N-diethylamino)diazenium-1,2-diolate (diethylamine NONOate or "DEA/NO") and derivatives thereof. NONOates are also described in U.S. Pat. Nos. 6,232,336; 5,910,316 and 5,650,447. The "NO adducts" can be mono-nitrosylated, poly-nitrosylated, mono-nitrosated and/or poly-nitrosated at a variety of naturally susceptible or artificially provided binding sites for biologically active forms of nitrogen monoxide.

Suitable furoxanes include, but are not limited to, CAS 1609, C93-4759, C92-4678, S35b, CHF 2206, CHF 2363, and the like.

Suitable sydnonimines include, but are not limited to, molsidomine (N-ethoxycarbonyl-3-morpholinosydnonimine), SIN-1(3-morpholinosydnonimine) CAS 936 (3-(cis-2,6-dimethylpiperidino)-N-(4-methoxybenzoyl)-sydnonimine, pirsidomine), C87-3754 (3-(cis-2,6-dimethylpiperidino)-N-sydnonimine, linsidomine, C4144 (3-(3,3-dimethyl-1,4 thiazane-4-yl)sydnonimine hydrochloride), C89-4095 (3-(3,3-dimethyl-1,1-dioxo-1,4-thiazane-4-yl)sydnonimine hydrochloride, and the like.

Suitable oximes, include but are not limited to, NOR-1, NOR-3, NOR-4, and the like.

One group of NO adducts is the S-nitrosothiols, which are compounds that include at least one —S—NO group. These compounds include S-nitroso-polypeptides (the term "polypeptide" includes proteins and polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars; S-nitrosylated, modified and unmodified, oligonucleotides (preferably of at least 5, and more preferably 5-200 nucleotides); straight or branched, saturated or unsaturated, aliphatic or aromatic, substituted or unsubstituted S-nitrosylated hydrocarbons; and 5-nitroso heterocyclic compounds. S-nitrosothiols and methods for preparing them are described in U.S. Pat. Nos. 5,380,758 and 5,703,073; WO 97/27749; WO 98/19672; and Oae et al, Org. Prep. Proc. Int (3): 165-198 (1983), the disclosures of each of which are incorporated by reference herein in their entirety.

Another embodiment of the invention is S-nitroso amino acids where the nitroso group is linked to a sulfur group of a sulfur-containing amino acid or derivative thereof. Such compounds include, for example, S-nitroso-N-acetylcysteine, S-nitroso-captopril, S-nitroso-N-acetyl penicillamine, S-nitroso-homocysteine, S-nitroso-cysteine, S-nitroso-glutathione, S-nitroso-cysteinyl-glycine, and the like.

Suitable S-nitrosylated proteins include thiol-containing proteins (where the NO group is attached to one or more sulfur groups on an amino acid or amino acid derivative thereof) from various functional classes including enzymes, such as tissue-type plasminogen activator (TPA) and cathepsin B; transport proteins, such as lipoproteins; heme proteins, such as hemoglobin and serum albumin; and biologically protective proteins, such as immunoglobulins, antibodies and cytokines. Such nitrosylated proteins are described in WO 93/09806, the disclosure of which is incorporated by reference herein in its entirety.

Examples include polynitrosylated albumin where one or more thiol or other nucleophilic centers in the protein are modified.

Other examples of suitable S-nitrosothiols include:

  (i)

  (ii)

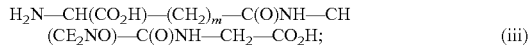  (iii)

wherein m is an integer from 2 to 20.

$R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, a cycloalkylalkyl, a cycloalkylthio, an arylalklyfhio, an arylalkdythioalkyl, an alkylthioalkyl a cycloalkenyl, an heterocyclicalkyl, an alkoxy, a haloalkoxy, an amino, an alkylamino, a dialkylamino, an arylamino, a diarylamino, an alkylarylamino, an alkoxyhaloalkyl, a sulfonic acid, a sulfonic ester, an alkylsulfonic acid, an arylsulfonic acid, an arylalkoxy, an alkylthio, an arylthio, a cyano an aminoalkyl, an aminoaryl, an aryl, an arylalkyl, an alkylaryl, a carboxamido, a alkylcarboxamido, an arylcarboxamido, an amidyl, a carboxyl, a carbamoyl, an alkylcarboxylic acid, an arylcarboxylic acid.

$R_1$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylaryl, an alkylsulfinyl, an alkylsulfonyl, an alkylsulfonyloxy, an arylsulfinyl, an-arylsulfonyl, arylsulphonyloxy, a sulfonamido, a carboxamido, a carboxylic ester, an aminoalkyl, an aminoary

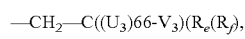

a bond to an adjacent atom creating a double bond to that atom, $—(N_2O_2—)-M_1+$, wherein $M_1+$ is an organic or inorganic cation.

In cases where $R_e$ and $R_f$ are a heterocyclic ring or taken together $R_e$ and $R_f$ are a heterocyclic ring, then $R_1$ can be a substituent on any disubstituted nitrogen contained within the radical wherein $R_+$ is as defined herein.

Nitrosothiols can be prepared by various methods of synthesis. In general, the thiol precursor is prepared first, then converted to the S-nitrosothiol derivative by nitrosation of the thiol group with $N_aNO_2$ under acidic conditions (pH is about 2.5) which yields the S-nitroso derivative. Acids which can be used for this purpose include aqueous sulfuric, acetic and hydrochloric acids. The thiol precursor can also be nitrosylated by reaction with an organic nitrite such as tert-butyl nitrite, or a nitrosonium salt such as nitrosonium tetrafluoroborate in an inert solvent.

Another group of NO adducts for use in the invention, where the NO adduct is a compound that donates, transfers or releases nitric oxide, include compounds comprising at least one ON—O— or ON—N— group. The compounds that include at least one ON—O— or ON—N— group are preferably ON—O— or ON—N— polypeptides (the term "polypeptide" includes proteins and polyamino acids that do not possess an ascertained biological function, and derivatives thereof); ON—O— or ON—N— amino acids (including natural and synthetic amino acids and their stereoisomers and racemic mixtures); ON—O— or ON—N— sugars; ON—O— or —ON—N— modified or unmodified oligonucleotides (comprising at least 5 nucleotides, preferably 5-200 nucleotides); ON—O— or ON—N— straight or branched, saturated or unsaturated, aliphatic or aromatic, substituted or unsubstituted hydrocarbons; and ON—O—, ON—N— or ON—C-heterocyclic compounds. Preferred examples of compounds comprising at least one ON—O— or ON—N— group include butyl nitrite, isobutyl nitrite, tert-butyl nitrite, amyl nitrite, isoamyl nitrite, N-nitrosamines, N-nitrosamides, N-nitrosourea, N-nitrosoguanidines, N-nitrosocarbamates, N-acyl-N-nitroso compounds (such as, N-methyl-N-nitrosourea); N-hydroxy-N-nitrosamines, cupferron, alanosine, dopastin, 1,3-disubstituted nitrosiminobenzimidazoles, 1,3,4-thiadiazole-2-nitrosimines, benzothiazole-2(3H)-nitrosimines, thiazole-2-nitrosimines, oligonitroso sydnonimines, 3-alkyl-N-nitroso-sydnonimines, 2H-1,3,4-thiadiazine nitrosimines.

Another group of NO adducts for use in the invention include nitrates that donate, transfer or release nitric oxide, such as compounds comprising at least one $O_2N—O—$, $O_2N—N—$ or $O_2N—S—$ group. Preferred among these compounds are $O_2N—O—$, $O_2N—N—$ or $O_2N—S—$ polypeptides (the term "polypeptide" includes proteins and also polyamino acids that do not possess an ascertained biological function, and derivatives thereof); $O_2N—O—$, $O_2N—N—$ or $O_2N—S—$ amino acids (including natural and synthetic amino acids and their stereoisomers and racemic mixtures); $O_2N—O—$, $O_2N—N—$ or $O_2N—S—$ sugars; $O-_2N—O—$, $O_2N—N—$ or $O_2N—S—$ modified and unmodified oligonucleotides (comprising at least 5 nucleotides, preferably 5-200 nucleotides); $O_2N$—O—, $O_2N$—N— or $O_2N$—S— straight or branched, saturated or unsaturated, aliphatic or aromatic, substituted or unsubstituted hydrocarbons; and $O_2N$—O—, $O_2N$—N— or $O_2N$—S-heterocyclic compounds. Preferred examples of compounds comprising at least one $O_2N$—O—, $O_2N$—N— or $O_2N$—S— group include isosorbide dinitrate, isosorbide mononitrate, clonitrate, erythrityl tetranitrate, mannitol hexanitrate, nitroglycerin, pentaerythritoltetranitrate, pentrinitrol, propatylnitrate and organic nitrates with a sulfhydryl-containing amino acid such as, for example SPM 3672, SPM 5185, SPM 5186 and those disclosed in U.S. Pat. Nos. 5,284,872, 5,428,061, 5,661,129, 5,807,847 and 5,883, 122 and in WO 97/46521, WO 00/54756 and in WO 03/013432.

Another group of NO adducts are N-oxo-N-nitrosoamines that donate, transfer or release nitric oxide and are represented by the formula:

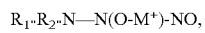

where $R_{1''}$ and $R_{2''}$ are each independently a polypeptide, an amino acid, a sugar, a modified or unmodified oligonucleotide, a straight or branched, saturated or unsaturated, aliphatic or aromatic, substituted or unsubstituted hydrocarbon, or a heterocyclic group, and where $M_1^+$ is an organic or inorganic cation, such, as for example, an alkyl substituted ammonium cation or a Group I metal cation.

When administered separately, the amino acid ester compound comprising a nitric oxide releasing group and/or nitric oxide donor can be administered about the same time as part of the overall treatment regimen, i.e., as a combination therapy. "About the same time" includes administering the one amino acid ester compound comprising a nitric oxide releasing group, simultaneously, sequentially, at the same time, at different times on the same day, or on different days, as long as they are administered as part of an overall treatment regimen, i.e., combination therapy or a therapeutic cocktail.

When administered in vivo, the compounds and compositions of the invention can be administered in combination with pharmaceutically acceptable carriers and in dosages described herein. When the compounds and compositions of the invention are administered as a combination of at least one amino acid ester compound comprising a nitric oxide releasing group and/or at least one nitric oxide donor, they can also be used in combination with one or more additional compounds such as creatine, creatine precursors, creatine derivatives and/or combinations thereof, or aphrodisiac compounds. The nitric oxide donors and other additional compounds can be administered simultaneously with, subsequently to, or prior to administration of the amino acid ester compound comprising a nitric oxide releasing group.

The compounds and compositions of the invention can be administered by any available and effective delivery system including, but not limited to, orally, bucally, parenterally, by inhalation, by topical application, by injection, transdermally, or rectally (e.g., by the use of suppositories) in dosage unit formulations containing conventional nontoxic pharmaceutically acceptable carriers, adjuvants, and vehicles, as desired. Parenteral includes subcutaneous injections, intravenous, intramuscular, intrasternal injection, or infusion techniques. In one embodiment of the invention the amino acid ester compound comprising at least one nitric oxide releasing group is administered orally, parentally or by inhalation.

Transdermal compound administration, which is known to one skilled in the art, involves the delivery of pharmaceutical compounds via percutaneous passage of the compound into the systemic circulation of the patient. Topical administration can also involve the use of transdermal administration such as transdermal patches or iontophoresis devices. Other components can be incorporated into the transdermal patches as well. For example, compositions and/or transdermal patches can be formulated with one or more preservatives or bacteriostatic agents including, but not limited to, methyl hydroxybenzoate, propyl hydroxybenzoate, chlorocresol, benzalkonium chloride, and the like. Dosage forms for topical administration of the compounds and compositions can include creams, sprays, lotions, gels, ointments, eye drops, nose drops, ear drops, and the like. In such dosage forms, the compositions of the invention can be mixed to form white, smooth, homogeneous, opaque cream or lotion with, for example, benzyl alcohol 1% or 2% (wt/wt) as a preservative, emulsifying wax, glycerin, isopropyl palmitat, lactic acid, purified water and sorbitol solution. In addition, the compositions can contain polyethylene glycol 400. They can be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g., gauze, can be impregnated with the compositions in solution, lotion, cream, ointment or other such form can also be used for topical application. The compositions can also be applied topically using a transdermal system, such as one of an acrylic-based polymer adhesive with a resinous crosslinking agent impregnated with the composition and laminated to an impermeable backing.

The compositions can also be applied topically using a transdermal system, such as one of an acrylic-based polymer adhesive with a resinous crosslinking agent impregnated with the composition and laminated to an impermeable backing. In a particular embodiment, the compositions of the invention are administered as a transdermal patch, more particularly as a sustained-release transdermal patch. The transdermal patches of the invention can include any conventional form such as, for example, adhesive matrix, polymeric matrix, reservoir patch, matrix or monolithic-type laminated structure, and are generally comprised of one or more backing layers, adhesives, penetration enhancers, an optional rate controlling membrane and a release liner which is removed to expose the adhesives prior to application. Polymeric matrix patches also comprise a polymeric-matrix forming material. Suitable transdermal patches are described in more detail in, for example, U.S. Pat. Nos. 5,262,165; 5,948,433; 6,010,715 and 6,071,531.

Solid dosage forms for oral administration can include capsules, sustained-release capsules, tablets, sustained release tablets, chewable tablets, sublingual tablets, effervescent tablets, pills, powders, granules and gels. In such solid dosage forms, the active compounds can be admixed with at least one inert diluent such as sucrose, lactose or starch. Such dosage forms can also comprise, as in normal practice, additional substances other than inert diluents, e.g., lubricating agents such as magnesium stearate. In the case of capsules, tablets, effervescent tablets, and pills, the dosage forms can also comprise buffering agents. Soft gelatin capsules can be prepared to contain a mixture of the active compounds or compositions of the invention and vegetable oil. Hard gelatin capsules can contain granules of the active compound in combination with a solid, pulverulent carrier such as lactose, saccharose, sorbitol, mannitol, potato starch, corn starch, amylopectin, cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Suppositories for vaginal or rectal administration of the compounds and compositions of the invention, such as for treating pediatric fever and the like, can be prepared by mixing the compounds or compositions with a suitable nonirritating excipient such as cocoa butter and polyethylene glycols which are solid at room temperature but liquid at rectal temperature, such that they will melt in the rectum and release the drug.

Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution.

The compositions of this invention can further include conventional excipients, i.e., pharmaceutically acceptable organic or inorganic carrier substances suitable for parenteral application which do not deleteriously react with the active compounds. Suitable pharmaceutically acceptable carriers include, for example, water, salt solutions, alcohol, vegetable oils, polyethylene glycols, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/or dextran. Optionally, the suspension may also contain stabilizers.

The composition, if desired, can also contain minor amounts of wetting agents, emulsifying agents and/or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, and the like.

Various delivery systems are known and can be used to administer the compounds or compositions of the invention, including, for example, encapsulation in liposomes, microbubbles, emulsions, microparticles, microcapsules and the like. The required dosage can be administered as a single unit or in a sustained release form.

The bioavailability of the compositions can be enhanced by micronization of the formulations using conventional techniques such as grinding, milling, spray drying and the like in the presence of suitable excipients or agents such as phospholipids or surfactants.

Sustained release dosage forms of the invention may comprise microparticles and/or nanoparticles having a compound of interest dispersed therein or may comprise the compound in pure, preferably crystalline, solid form. For sustained release administration, microparticle dosage forms comprising pure, preferably crystalline, compound are preferred. The therapeutic dosage forms of this aspect of the invention may be of any configuration suitable for sustained release.

Nanoparticle sustained release therapeutic dosage forms are preferably biodegradable and, optionally, bind to the vascular smooth muscle cells and enter those cells, primarily by endocytosis. The biodegradation of the nanoparticles occurs over time (e.g., 30 to 120 days; or 10 to 21 days) in prelysosomic vesicles and lysosomes. Preferred larger microparticle therapeutic dosage forms of the invention release the compound of interest for subsequent target cell uptake with only a few of the smaller microparticles entering the cell by phagocytosis. A practitioner in the art will appreciate that the precise mechanism by which a target cell assimilates and metabolizes a dosage form of the invention depends on the morphology, physiology and metabolic processes of those cells. The size of the particle sustained release therapeutic dosage forms is also important with respect to the mode of cellular assimilation. For example, the smaller nanoparticles can flow with the interstitial fluid between cells and penetrate the infused tissue. The larger microparticles tend to be more easily trapped interstitially in the infused primary tissue, and thus are useful to deliver compounds of interest.

Particular sustained release dosage forms of the invention comprise biodegradable microparticles or nanoparticles. More particularly, biodegradable microparticles or nanoparticles are formed of a polymer containing matrix that biodegrades by random, nonenzymatic, hydrolytic scissioning to release a compound of interest, thereby forming pores within the particulate structure.

In a particular embodiment, the compositions of the invention are administered parenterally or orally as a sustained release tablet or a sustained release capsule. For example, the parental or sustained release formulations can comprise a therapeutically effective amount of at least one amino acid ester compound comprising a nitric oxide releasing group or a pharmaceutically acceptable salt thereof, and, optionally at least one nitric oxide donor, or the parental or sustained release formulations can comprise a therapeutically effective amount of at least one amino acid ester compound comprising a nitric oxide releasing group or a pharmaceutically acceptable salt thereof, and at least one nitric oxide donor, and, optionally at least one compound of interest.

The compounds and compositions of the invention can be formulated as pharmaceutically acceptable salt forms. Pharmaceutically acceptable salts include, for example, alkali metal salts and addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids include, but are not limited to, hydrochloric, hydrobromic, hydroiodic, nitric, carbonic, sulfuric and phosphoric acid and the like. Appropriate organic acids include, but are not limited to, aliphatic, cycloaliphatic, aromatic, heterocyclic, carboxylic and sulfonic classes of organic acids, such as, for example, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, algenic, β-hydroxybutyric, cyclohexylaminosulfonic, galactaric and galacturonic acid and the like. Suitable pharmaceutically-acceptable base addition salts include, but are not limited to, metallic salts made from aluminum, calcium, lithium, magnesium, potassium, sodium and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound. In one embodiment, the pharmaceutically acceptable salts of the compounds of the invention include the nitrate salts. In another embodiment, the pharmaceutically acceptable salts of the compounds of the invention are heterocyclic compounds such as, furoxan, a sydnonimine, an oxatriazole-5-one and/or an oxatriazole-5-imine.

While individual needs may vary, determination of optimal ranges for effective amounts of the compounds and/or compositions is within the skill of the art. Generally, the dosage required to provide an effective amount of the compounds and compositions, which can be adjusted by one of ordinary skill in the art, will vary depending on the age, health, physical condition, sex, diet, weight, extent of the dysfunction of the recipient, frequency of treatment and the nature and scope of the dysfunction or disease, medical condition of the patient, the route of administration, pharmacological considerations such as the activity, efficacy, pharmacokinetic and toxicology profiles of the particular compound used, whether a drug delivery system is used, and whether the compound is administered as part of a drug combination.

The amount of a given amino acid ester compound comprising a nitric oxide releasing group of the invention that will be effective in the treatment of a particular disorder or condition will depend on the nature of the disorder or condition, and can be determined by standard clinical techniques, including reference to Goodman and Gilman, supra; The Physician's Desk Reference, Medical Economics Company, Inc., Oradell, N.J., 1995; and Drug Facts and Comparisons, Inc., St. Louis, Mo., 1993. The precise dose to be used in the formulation will also depend on the route of administration, and the seriousness of the disease or disorder, and should be decided by the physician and the patient's circumstances.

In one embodiment of the invention the amino acid ester compound comprising a nitric oxide releasing group is administered as a daily dose of about 0.01 mg to about 20 mg, preferably at a daily dose of about 0.1 to 15 mg and even more preferably at a daily dose of about 0.3 to 10 mg. The administration may be as a single dose or as an initial bolus followed by continuous infusion of the remaining portion of a complete dose over time.

The compounds and compositions of the invention can be formulated as supplements for use by man to supplement the diet by increasing the total daily intake, or a concentrate, metabolite, constituent, extract, or combinations of these ingredients. Such a supplement can bear or contain one or more of the following dietary ingredients: a vitamin, a mineral, an herb or other botanical, an amino acid and a dietary substance.

The invention also provides pharmaceutical kits comprising one or more containers filled with one or more of the ingredients of the pharmaceutical compounds and/or compositions of the invention, including, at least, one or more of the novel amino acid ester compound comprising at least one nitric oxide releasing group, and one or more of the vasodilators described herein. Associated with such kits can be additional compounds of interest.

ALTERNATIVE EMBODIMENTS

Combination of the Composition with One or More Additional Compounds

A novel nitric oxide "universal" donor consisting of an amino acid molecule or of an acetylated, methylated or modified amino acid molecule linked by an ester linkage to a nitroxy alcohol has been developed. This molecule can be used not only as a single supplement for nitric oxide release, but also in combination with a large number of compounds such as creatine and aphrodisiac compounds for example.

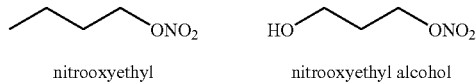

nitrooxyethyl      nitrooxyethyl alcohol

Amino Acid Ester Derivatives Liberating Nitric Oxide

C2 and C3 derivatives of the amino acid ethyl esters are developed to produce an ester linkage at the COOH with O—NO$_2$ thru either the ethyl or propyl groups. There are many different possibilities to block the NH$_2$ of the amino acid ester molecule, such as the use of malate, hydroxycitronate, citrate, glycerol and diglcerol for example. Many different moieties are linked to the anhydride group. The amino acid ethyl ester was used as the most desirable due to solvent choice and final lipophilicity, stability and absorption for sublingual delivery.

Nitroacetylchloride Condensation with Amino Acid Ester Ethyl Ester

Synthesis of Composition

The nitro amino acid esters can be derived from the NH$_2$ linkage to form amides or from the carboxyl end to derive esters. Also, they can even be both on the same double hybrid molecule. The reactions are through mononitrate intermediates such as nitroacetylchloride for the amide linkage, and simple ester linkages on the carboxyl.

Example I

Step 1

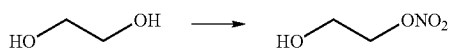

It is well known that the mononitration of alcohols can be usually carried out with concentrated nitric acid. Thus 2-hydroxyethyl nitrate (nitrooxyethanol), a known compound, was prepared through the reaction of concentrated nitric acid and 1,2-ethanediol. The reaction was carefully monitored and the product was extracted, washed, dried and directly used in the following reaction.

Step 2

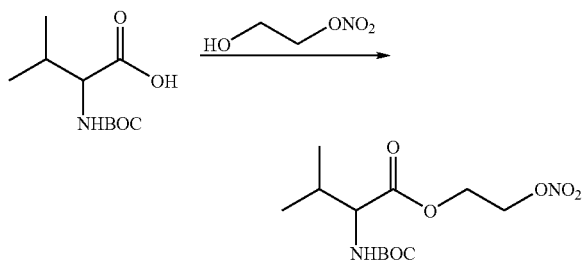

The ester formation can be achieved with different reagents, such as commonly used DCC and EDC. Different conditions have been used, and the following is one specific example.

To the reactor 2-hydroxyethyl nitrate (8 kg) was added, followed by dichloromethane (25 L). Then, boc-L-valine (12.5 kg) was added slowly under stirring, and the reaction mixture was cooled down to −10° C. Afterwards, DMAP (50 g) was added as the catalyst, and DCC (12.5 kg dissolved in 5 L of dichloromethane) was slowly added dropwise to the mixture under −10° C. The reaction was continued for another 5 hours at temperature between −10 and 0° C. under continuous stirring, while insoluble white solid was gradually formed. The reaction mixture was then warmed up slowly to room temperature, and the reaction was continued for another 12 hours at room temperature. At the end, the reaction mixture was filtered, and the filtrate was washed with water and dried to yield the crude nitrooxyethyl boc-valinate that was used directly in the next step.

Step 3

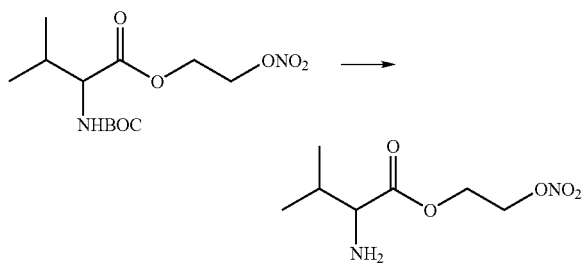

Add ethyl acetate (25 L) and hydrochloride (9 L) separately to the product of Step 2, crude nitrooxyethyl boc-valinate, and the mixture was stirred for 10 hours. After the reaction, concentrated sodium hydroxide was added dropwise to adjust the pH to 9 under strong stirring. The mixture was then separated, and the organic phase was washed with saturated NaCl solution (10L) a few times.

Step 4

Purification of Nitrooxyethyl Valinate

Due to the nature of the product, nitrooxyethyl valinate, the solution obtained at Step 3 was purified by a series of acid-base treatments, and each step was monitored, the final organic phase was washed with saturated NaCl solution a few times, and dried over MgSO$_4$ powder and filtered. The filtrate solution was then dried by rotary evaporation to yield light yellowish oil as the final product (8 kg).

Step 5

Formation of Salt

The product, nitrooxyethyl valinate has an amino group in its structure, thus it can form all kinds of salts with different acids. These acids include organic acids such as acetic acid, and inorganic acid such as hydrochloric acid. Such a salt may be further purified by re-crystallization.

Structure of the Composition

The embodiments and examples presented herein are illustrative of the general nature of the subject matter claimed and are not limiting. It will be understood by those skilled in the art how these embodiments can be readily modified and/or adapted for various applications and in various ways without departing from the spirit and scope of the subject matter disclosed claimed.

The claims hereof are to be understood to include without limitation all alternative embodiments and equivalents of the subject matter hereof. Phrases, words and terms employed herein are illustrative and are not limiting. Where permissible by law, all references cited herein are incorporated by reference in their entirety. It will be appreciated that any aspects of the different embodiments disclosed herein may be combined in a range of possible alternative embodiments, and alternative combinations of features, all of which varied combinations of features are to be understood to form a part of the subject matter claimed.

What is claimed is:

1. A compound of the formula

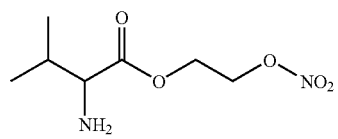

2′-nitrooxyethyl 2-amino-3-methylbutanoate, or a pharmaceutically acceptable salt thereof.

2. A composition for increasing nitric oxide physiological levels in a subject, which comprises a therapeutically effective amount of the compound of claim 1 or a pharmaceutically acceptable salt thereof and a pharmaceutically acceptable carrier.

3. The composition according to claim 2, wherein said pharmaceutically acceptable carrier is chosen from, propylene glycol monocaprylate, propylene glycol, water, sodium lauryl sulfate, salt solutions, alcohol, vegetable oils, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose and polyvinylpyrrolidon.

4. The composition according to claim 2, wherein said pharmaceutically acceptable carrier is saliva-absorbing microcrystalline cellulose.

5. The composition according to claim 2, which is formulated as a liquid formulation, a liquid dosage form, an enteric-coated soft-gel capsule, a capsule, a sustained-release capsule, a tablet, a sustained release tablet, a chewable tablet, a sublingual tablet, an effervescent tablet, a pill, powders, granules, gels and suppositories.

6. The composition according to claim 2, which further comprises creatine.

7. The composition according to claim 2, further comprising a vasodilatory compound chosen from L-arginine, norvaline, and citrulline.

8. A method for increasing nitric oxide physiological levels in a subject, which comprises administering a sufficient amount of the composition of claim 2.

9. The method according to claim 8, wherein said administration is oral, bucal, parenteral, transdermal, rectal, by inhalation, by topical application or by injection.

10. The method according to claim 8, wherein said administration is oral.

11. The method according to claim 8, wherein said amount is a daily total dosage of about 0.05 to 1000 mg.

12. The method according to claim 11, wherein said daily total dosage is administered at least once a day.

* * * * *